United States Patent
Mills et al.

[11] Patent Number: 5,971,975
[45] Date of Patent: Oct. 26, 1999

[54] GUIDE CATHETER WITH ENHANCED GUIDEWIRE TRACKING

[75] Inventors: Timothy C. Mills, Los Gatos; Rhoda M. Santos, Newark; Erik T. Engelson, Menlo Park; Henry Nita, Milpitas, all of Calif.

[73] Assignee: Target Therapeutics, Inc., Fremont, Calif.

[21] Appl. No.: 08/729,237

[22] Filed: Oct. 9, 1996

[51] Int. Cl.$^6$ .................................................. A61M 25/00
[52] U.S. Cl. ............................................ 604/527; 604/525
[58] Field of Search .................................... 604/264, 280, 604/282; 128/656–658; 138/123, 127, 129, 133, 138, 174

[56] References Cited

U.S. PATENT DOCUMENTS

| | | |
|---|---|---|
| 243,396 | 6/1881 | Pfarre . |
| 2,211,975 | 8/1940 | Hendrickson . |
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |
| 4,430,083 | 2/1984 | Ganz et al. . |
| 4,484,586 | 11/1984 | McMickle et al. . |
| 4,516,972 | 5/1985 | Samson . |
| 4,657,024 | 4/1987 | Coneys . |
| 4,676,229 | 6/1987 | Krasnicki et al. . |
| 4,737,153 | 4/1988 | Shimamura et al. . |
| 4,739,768 | 4/1988 | Engelson . |
| 4,806,182 | 2/1989 | Rydell et al. . |
| 4,832,681 | 5/1989 | Lenck . |
| 4,899,787 | 2/1990 | Ouchi et al. . |
| 4,981,478 | 1/1991 | Evard et al. . |
| 4,985,022 | 1/1991 | Fearnot et al. . |
| 5,037,404 | 8/1991 | Gold et al. . |
| 5,057,092 | 10/1991 | Webster, Jr. . |
| 5,069,674 | 12/1991 | Fearnot et al. . |
| 5,176,660 | 1/1993 | Truckai . |
| 5,178,158 | 1/1993 | de Toledo . |
| 5,180,376 | 1/1993 | Fischell . |
| 5,217,482 | 6/1993 | Keith . |
| 5,222,949 | 6/1993 | Kaldany . |
| 5,248,305 | 9/1993 | Zdrahala . |
| 5,313,967 | 5/1994 | Lieber et al. . |
| 5,405,338 | 4/1995 | Kranys . |
| 5,531,721 | 7/1996 | Pepin et al. . |

FOREIGN PATENT DOCUMENTS

| | | |
|---|---|---|
| 0098100 | 1/1984 | European Pat. Off. . |
| 0421650 | 4/1991 | European Pat. Off. . |
| 0594201 | 4/1994 | European Pat. Off. . |
| 0643979 | 3/1995 | European Pat. Off. . |
| 2613231 | 10/1988 | France . |
| 3642107 | 6/1987 | Germany . |
| 2-283346 | 11/1990 | Japan . |
| 3-23830 | 1/1991 | Japan . |
| 5-56910 | 3/1993 | Japan . |
| 5-220225 | 8/1993 | Japan . |
| WO 92/07507 | 5/1992 | WIPO . |
| WO 93/05842 | 4/1993 | WIPO . |
| WO 93/15785 | 8/1993 | WIPO . |
| WO 94/00174 | 1/1994 | WIPO . |
| WO 95/13110 | 5/1995 | WIPO . |

*Primary Examiner*—Corrine McDermott
*Attorney, Agent, or Firm*—Morrison & Foerster LLP

[57] ABSTRACT

This is a guide catheter assembly. The guide catheter assembly is used to cooperate with a micro-catheter in accessing a tissue target within the body, typically a target which is accessible through the vascular system. Central to the invention is the use of a braided metallic reinforcing member, situated within the catheter body in such a way to create a catheter section having an exceptionally thin wall, controlled stiffness, and high resistance to kinking. The catheter has a terminal segment which is not supported by a braid and the polymer making up that terminal segment is either the same hardness as is the polymer making up the outer covering of next more adjacent section or, preferably, the polymer is harder than is the polymer making up the segment located just proximally of that terminal segment. The braid may have a single pitch or may vary in pitch along the axis of the catheter or catheter section. The braided reinforcing member typically is embedded in a flexible outer tubing member. An inner tubing member is lubricious.

16 Claims, 3 Drawing Sheets

GUIDE CATHETER WITH ENHANCED GUIDEWIRE TRACKING

FIELD OF THE INVENTION

This invention is a surgical device. In particular, it is a guide catheter assembly. The guide catheter assembly is used to cooperate with a micro-catheter in accessing a tissue target within the body, typically a target which is accessible through the vascular system. Central to the invention is the use of a braided metallic reinforcing member, situated within the catheter body in such a way to create a catheter section having an exceptionally thin wall, controlled stiffness, and high resistance to kinking. The catheter has a terminal segment which is not supported by a braid and the polymer making up that terminal segment is of equal hardness to or is harder than the polymer of the segment located just proximally. The braid may have a single pitch or may vary in pitch along the axis of the catheter or catheter section. The braided reinforcing member typically is embedded in a flexible outer tubing member. An inner tubing member is lubricious. The terminal segment may also have a smaller diameter than does its more proximal regions.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of circulatory system diseases is via angioplasty (PCA). Such a procedure uses catheters having balloons on their distal tips. It is similarly common that those catheters are used to deliver a radio-opaque agent to the site in question prior to the PCA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered. Flow-directed catheters are rarely used as guide catheters.

This inventive catheter is used to direct a smaller catheter from a body entry site to a site intermediate to the treatment site. The use of this catheter extends the site at which smaller catheter first enters the bloodstream.

This invention is an adaptable one and may be used in a variety of catheter formats. The invention utilizes the concept of combining one or more polymeric tubes with a metallic braid comprising wires or ribbons of a stainless steel or super-elastic alloy. The construction technique has the benefit of producing catheter sections having small overall diameters but with exceptional strength, resistance to kinking, and recovery from kinking (even in vivo) should such kinking occur.

The use of braids in a catheter body is not a novel concept. Typical background patents are discussed below. However, none of these documents have used our concept to produce a catheter which has the physical capabilities of the catheter of this invention.

Multi-Wrap Catheters

There are a number of catheters discussed in the literature which utilize catheter bodies having multiply-wrapped reinforcing material. These catheters include structures having braided bands or ones in which the spirally wound material is simply wound in one direction and the following layer or layers are wound in the other.

Crippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. The device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is a polyaramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to de Toledo, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,567,024, to Coneys, shows a catheter which employs a set of helical strips within the wall of the catheter. However, the helical strips are of a radio-opaque material, e.g., fluorinated ethylene-propylene. It is not clear that the blended radio-opaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy". The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end.

U.S. Pat. No. 5,313,967, to Lieber et al., shows a medical device, a portion of which is a helical coil which apparently may include an outer plastic sheath in some variations. Apparently, a secondary helix of a somewhat similar design (in that it is formed by rotating a flat wire or the like along its longitudinal axis to form a screw-like configuration) is included within the helical coil to provide axial pushability and torque transmission.

U.S. Pat. No. 5,405,338, to Kranys, describes a helically wound catheter incorporating a shaft component having a helically wound coil with a skin or webbing supported by the coil. The skin or webbing is said to contribute "negligibly to the resistance of the catheter to axially directed compressive forces . . . " The catheter may include an inner, taut skin component.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold."

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultra-thin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . . ". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described.

European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a medical probe used with an endoscope or for some other device used to stimulate the heart. The device appears to be a helix having a spacing between 0 and 0.25mm (See page 4, line 20) preferably rectangular in cross section (See Page 4, Line 1) and of a multiphase alloy such as M35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-kinking Configurations

U.S. Pat. No. 5,222,949, to Kaldany, describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher integral of cross-linking.

European Patent Application No. 0,421,650-A1 describes a method for producing a catheter from a roll of polymer film while incorporating other materials such as tinfoil elements or the like.

None of the documents cited above provides a structure required by the disclosure and claims recited below.

SUMMARY OF THE INVENTION

This invention includes a catheter section made up of an inner liner and an outer covering and having a braid located in that outer covering. The inner liner may be of a polymeric lubricious composition.

The braid, in its most basic form, comprises a number of small wires or ribbons wound and treated in such a way that the resulting braid is dimensionally stable and the braided ribbons do not twist. The more basic forms of braids used in this invention include those which are made up of an even number of equally sized members. Half of the members are woven in a clockwise direction (as viewed along the axis of the braid) and the remaining half are woven in a counter-clockwise direction. The various members may, of course, be of differing size but the sum of the members used in a particular direction should equal those wound in the other direction. Any imbalance will typically cause a helical curl in the resulting catheter. The alloys of choice are stainless steel although super-elastic alloys are also suitable. Nitinol is one such alloy. It is an alloy of nickel and titanium which is blended and heat treated in a specific way to produce an alloy having exceptional resistance to plastic deformation upon physical strain. Especially preferred liners comprise polytetrafluoroethylene (TFE) polymer. Hydrophilic coatings both on the interior and exterior are additionally contemplated.

This inventive catheter may include catheter sections with braids having more than one pitch or diameter or braid density in a section. The stiffness of the catheter section may be varied continuously by continuously varying the pitch or in a stepwise fashion by stepwise varying the pitch. The pitch may be varied during production of the braid or by changing the diameter of the braid after production. The braid may be partially constructed of polymeric fibers or carbon fibers either replacing a portion of the metallic ribbons or polymeric materials or placed in conjunction with a ribbon in the braid. Other metals, e.g., noble metals such as members of the platinum group or gold, may be used in the braid itself in much the same way to impart radio-opacity to the braid. To tailor the stiffness of the braid, the braid may first be wound and portions of the ribbon then removed. Also, the braid may be discontinuous.

The catheter has a terminal section which is solely polymeric and is of a polymer which is either harder than or is equal in hardness to the polymer in the next more proximal section. The outer covering is preferably a thermoplastic elastomer enclosing a braid. An inner liner of a lubricious material is also desirable. The terminal section may have a diameter less than that of the more proximal sections.

DESCRIPTION OF THE INVENTION

This catheter is a guide catheter. The catheter of this invention is used to guide other smaller catheters typically from an entry point in the human body to some intermediate point between that entry point and the site to be treated or studied. Guide catheters are typically, therefore, larger in outside and inside diameter than is the perfusion or balloon catheter which passes through it. It is often somewhat stiffer in overall flexibility so to pass through blood vessels having little curvature without significant assistance. Since the guide catheter is used as an adjunct to a separate smaller catheter, it is desirable that the guide catheter be able to go as far as is possible into the vasculature so to minimize the distance that the smaller catheter must then traverse. However, because guide catheters are sometimes used to pass between an entry site such as the femoral artery in the groin, through the trunk of the body, through the aortic arch, and into one of the various arteries stemming upward from the aortic arch, the tip of many guiding catheters is given a sharp or modest bend to allow it to pass into the ostium of those arteries without much assistance. Consequently, the stiffness needed to select the arterial ostium is contra to the goal of passing ever more distal into the vasculature. Inherent stiffness reduces the ability of the catheter both to follow a guidewire, when such is used, and secondly to pass into complicated and bending vasculature. We have found that by providing a short distal tip having a polymer which is the same hardness as or preferably is slightly harder, i.e., higher Shore number, than is the polymer in the next more proximal section, that the resulting tip provides significantly higher ease of penetrating into the vasculature and enhances its ability to follow and track a guidewire once into a vascular region where such a guidewire is desirable.

Figures 1, 2A, 2B, 3:
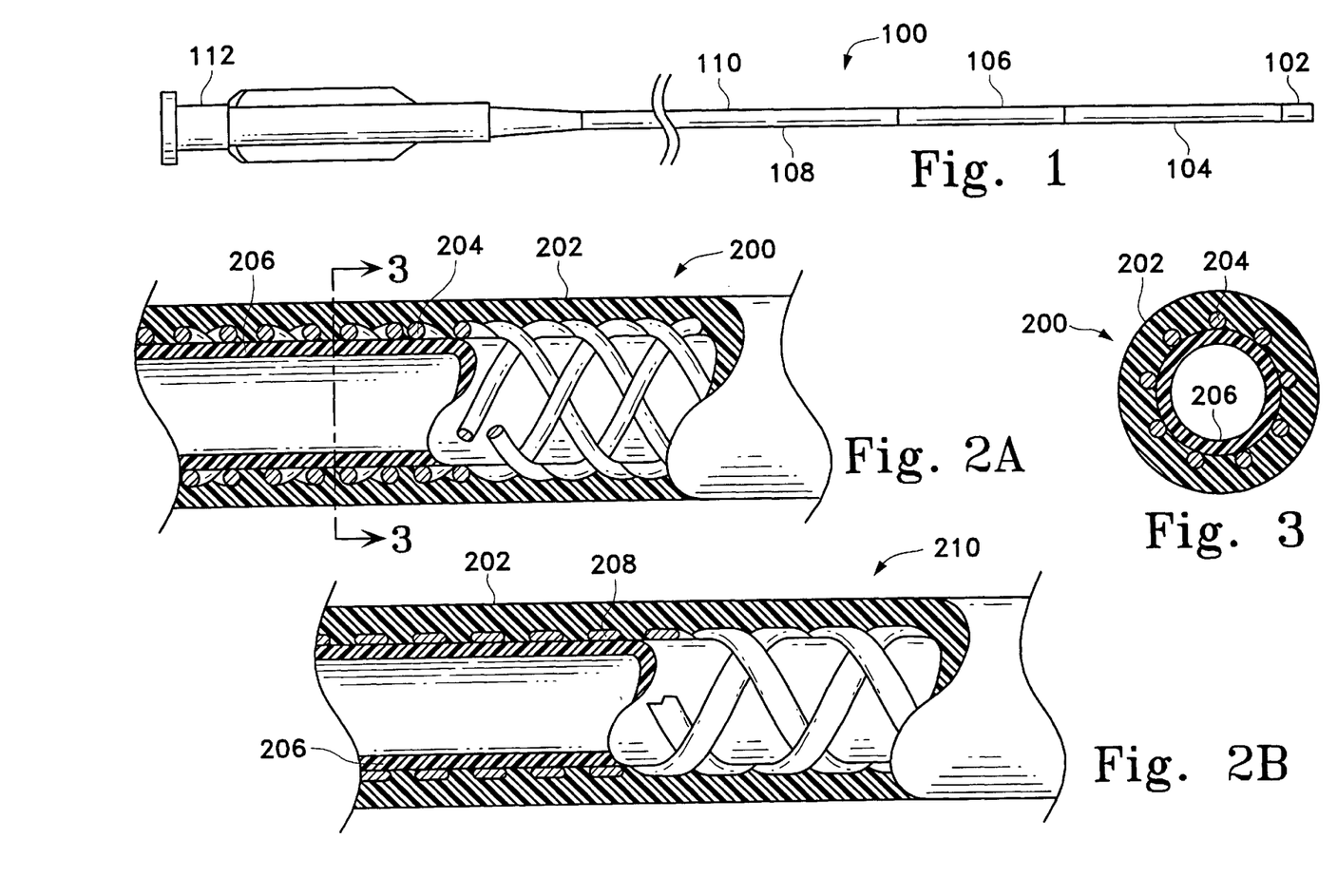
FIG. 1 shows, in side view, a typical catheter made using the concepts of this invention.
FIGS. 2A and 2B show, in magnification, partial, side view, cross-sections of the catheter sections made using this invention.
FIG. 3 shows, in magnification, partial, end view, cross-section of a catheter section made using this invention.

FIG. 1 shows a highly desirable variation (100) of the inventive catheter. In particular, the catheter includes at least three, and preferably four or more, sections which are supported by a metallic braid and a terminal portion which is not so supported. The polymer in the terminal portion (102) has the same or, preferably, higher Durometer value than the polymer in the outer layer of the next more proximal section adjacent it. For purposes of discussing this invention, the following conventions are used in describing the various sections: the most distal portion adjacent the terminal portion (102) is known as the distal segment (104). The next more proximal segment is known as the primary mid-section (106). The next more proximal section is known as the secondary mid-section (108). The most proximal and stiffest section is known simply as the proximal section (110). A through lumen extends from one end of the catheter to the other. A coupler of some type (112) is secured to the proximal end. The coupler (112) may be a manifold or "Y" type coupler. A sidearm of such coupler allows introduction of fluids such as radio-opacifiers into the lumen even as the inner catheter is passing through the guide catheter lumen. Obviously, some type of a seal may be included in the coupler to prevent leakage of bodily fluids from the proximal end of the catheter during use. Such seals, however, are not shown for the purpose of maintaining simplicity of the description of the invention. Radio-opaque bands may be independently placed within the catheter to show placement of various portions of the catheter. More desirable is the use of pacifiers which are added to the polymers. Suitable pacifiers include barium sulfate, bismuth trioxide, bismuth carbonate, powdered tungsten, powdered tantalum, or the like so that the location of various portions of the catheter may be visualized using a fluoroscope. It is desirable to vary the loading of dopant or radio-opacifier so that the various portions can be discriminated. The various portions or segments of the catheter which are proximal of terminal portion (102) are each made in a similar way although out of different materials.

FIGS. 2A and 2B show the two preferred ways of producing sections of the inventive catheter. Specifically, FIG. 2A shows an outer covering member (202) in which a wire based braid (204) is embedded. Interior to the section (200) is a lubricious inner layer (206). A number of these sections (200) are desirably assembled as shown in FIG. 2A and butted together as shown in FIG. 1 or may be formed so that the inner lubricious layer (206) and/or the wire braid (204) is continuous across two or more of the catheter sections (104, 106, 108, and 110 in FIG. 1).

FIG. 2B shows a variation of the inventive catheter section (210) in which the wire braid (204) is instead a ribbon braid (208). Again, lubricious inner liner (206) is seen therein. The ribbon braid (208) is embedded in the outer layer (202).

FIG. 3 shows a cross-sectional view of the variation (200) shown in FIG. 2A. Outer covering (202) is shown with the embedded wire braid (204) and the inner lubricious layer (206). FIG. 3 simply shows that the wire braid (204) is outside the outer diameter of the inner lubricious layer (206). Wire braid (204) (and its analog ribbon braid (208)) need not be completely covered on each of their respective surfaces by the material making up the outer surface (202), but it is desirable to let it do so.

The metallic braids (204, 208) are preferably made up of a number of metallic ribbons or wires, a majority of which comprise stainless steels (e.g., SS303, SS308, SS310, SS311, etc.).

Other highly desirable materials for those wires or ribbons are members of a class of alloys known as super-elastic alloys. Preferred super-elastic alloys include the class of titanium/nickel materials known generically as nitinol; alloys which were discovered by the U.S. Naval Ordnance Laboratory. These materials are discussed at length in U.S. Pat. No. 3,174,851 to Buehler et al., U.S. Pat. No. 3,351,463 to Rozner et al. and U.S. Pat. No. 3,753,700 to Harrison et al. Commercial alloys containing some amount, commonly up to about 5%, of one or more other members of the iron group, e.g., Fe, Cr, Co, etc., are considered to be encompassed within the class of super-elastic Ni/Ti alloys suitable for this service. When using a braid containing some amount of a super-elastic alloy, an additional step may be desirable to preserve the shape of the stiffening braid. For instance, with a Cr-containing Ni/Ti superelastic alloy which has been rolled into a 1×4 mil ribbon and formed into a 16-member braid, some heat treatment is desirable. The braid may be placed onto a, e.g., metallic mandrel, of an appropriate size and then heated to a temperature of 600° to 750° F. for a few minutes, to set the appropriate shape. After the heat treatment the braid (204, 208) retains its shape and the alloy retains its super-elastic properties.

Metallic ribbons that are suitable for use in the braid (208) of this invention desirably are between 0.25 mil and 3.5 mil in thickness and 2.5 mil and 12.0 mil in width. The term "ribbon" is meant to include elongated cross-sections such as a rectangle, oval, or semi-oval. When used as ribbons, these cross-sections should have an aspect ratio of thickness-width of at least 0.5.

It is within the scope of this invention that the ribbons or wires making up the braid (204, 208) also contain a minor amount of other materials. Fibrous materials, both synthetic and natural, may also be used. In certain applications, particularly smaller diameter catheter sections, more malleable metals and alloys, e.g., bold, platinum, palladium, rhodium, etc., may be used. A platinum alloy with a few percent of tungsten is sometimes preferred partially because of its radiopacity.

Suitable nonmetallic ribbons or wires include materials such as those made of polyaramides (Kevlar), polyethylene terephthalate (Dacron), or carbon fibers. The braids used in this invention may be made using commercial tubular braiders. The term "braid" is meant to include tubular constructions in which the ribbons making up the construction are woven in an in-and-out fashion as they cross, so as to form a tubular member defining a single lumen. The braid members may be woven in such a fashion that 2–4 braid members are woven together in a single weaving path. Typically, this is not the case. It is much more likely that a single-strand weaving path, as is shown in FIGS. 2A and 2B is used.

The braids shown in FIGS. 2A and 2B have a nominal pitch angle of 45°. Clearly the invention is not so limited. Other braid angles from 20° to 60° are also suitable. One important variation of this invention is the ability to vary the pitch angle of the braid either as the braid is woven or at the time the braid is included in catheter section or sections. The braid need not be continuous throughout the length of the catheter. In this way, the braid itself may be used to vary the flexibility of various sections of the catheter.

Referring again to FIGS. 2A and 2B, the materials of construction are as follows. Outer tube covering (202) desirably comprises a thermoplastic elastomer such as PEBAX or a polyurethane such as Pellethane (Dow Chemicals) and Carbothane (Thermedics). These materials are desirable because they are easily placed onto to the outside of the braiding by the laminating techniques described below. Nevertheless it may be desirable when producing a catheter such as that shown in FIG. 1A having sections of multiple flexibility to use materials having different moduli of flexibility and hardness (e.g., durometer values) such as discussed below. For instance, in the four flexibility section variation of a catheter assembly (100) shown in FIG. 1, the outer coverings for each of the sections may be a polymer of another family, e.g., polyolefins such as polyethylene (LLDPE and LDPE), polypropylene, with and without alloying of materials such as polyvinyl acetate or ethylvinyl acetate; polyesters such as various of the Nylons, polyethyleneterephthalate (PET); polyvinylchloride; polysulphones, including polyethersulphones, polyphenylsulphones; various ketone-based resins such as polyaryletheretherketone (PEEK) and variations of such as PEKK, PEKEKK; polyetheramides such as the polyether block amide sold as PEBAX by Atochem, and the like. These are suitable because they may be placed around the outer surface of the braid (204 in FIG. 2A and 208 in FIG. 2B). Stiffer materials might be placed in the region proximal on catheter assembly (100) shown in FIG. 1. More flexible materials might be placed on the exterior of section (106 and 108 in FIG. 1) and the most flexible on distal section (104) of FIG. 1. By varying the composition of the materials in this way, a catheter having fairly consistent outside diameter can be produced and yet have the desired flexibility. The most preferred polymeric material used in the outer surface assembly (202) are thermoplastic elastomers such as PEBAX.

Again, central to this invention is the use of a material in the terminal section (102 in FIG. 1) having a hardness greater than that of the material in the next more proximal section (104).

The inner liner (206) in the variations found in FIGS. 2A and 2B is preferably a lubricious material such as polytetrafluoroethylene or other appropriate fluorocarbon polymers, other lubricious polymers such as polyarylenes, and the like. Further, inner liner (206) may be a laminate of polyfluorocarbon on the interior and a polyurethane adjacent to the braid.

The polyetheramide and TFE combination is highly desirable, in that the outer surface of the TFE tubing employed may be chemically etched using solutions such as mixtures of metallic sodium and ammonia so that the TFE tubing will form a strong mechanical bond with adjacent polymers. When using the methodology described below, the preferred polyetheramide is melted into place using a temporary shrink wrap tubing as a forming member. The polymer flows through the interstices of the braid and bonds either to the etched polyfluorocarbon surface or to the polymer found on the other surface of the braid.

As noted above, each of the polymeric materials used in this inventive catheter may be filled with a radio-opaque filler material such as barium sulfate, bismuth trioxide, bismuth carbonate, powdered tungsten, powdered tantalum, or the like so that it will show up in some contrast to the materials which neighbor it. It is almost always desirable to be able to see, at least in a slight fashion, the outline of the catheter being introduced into the various regions of the body. It is to be appreciated that most of the tubing utilized in the devices of this invention is of such small size that fluoroscopy is otherwise unable to provide a good outline of those devices. Furthermore, it may be desirable in certain circumstances to differentiate between the various sections of the catheter by including differing amounts, loading, or types of radio-opaque fillers to different sections of the catheter.

Highly preferred for use of the inventive catheter as shown in FIG. 1 as a guiding catheter for introduction of a micro-catheter such as is shown in U.S. Pat. No. 4,739,768, to Engelson, or in U.S. patent application Ser. No. 08/641,259, to Samson et al, is the following:

| Section | length (cm) | preferred materials | Shore Hardness |
|---|---|---|---|
| 102 | 0.2–0.6 | PEBAX | 33D-37D |
| 104 | 5–9 | PEBAX | 30D-35D |
| 106 | 3–7 | PEBAX | 48D-55D |
| 108 | 1–9 | PEBAX | 60D-68D |
| 110 | 50–70 | NYLON11/ NYLON 12 | 72D-85D |

Each of these preferred materials is desirably infused with 25–55% barium sulfate radio-opacifier. The preferred material for inner layer (206) is a thin-walled (e.g., 0.001–0.0015") PTFE tubing of which the outer surface has been etched to provide a suitable bond with the outer layer (202). Typical outer diameters of the catheter are in the range of 0.065–0.100"; typical inner diameters are in the range of 0.048–0.082". The braid material is preferably 304SS wire with a diameter of 0.001 to 0.0015".

As noted above, the various sections of the catheter shown in FIG. 1 (104, 106, 108, and 110) are desirably made of the materials shown in either FIG. 2A or 2B and simply buttwelded together using heat. It is also desirable that the various outer coverings (202) for each of the sections be applied separately to a single interval braid (204 or 208) and inner liner (206).

Figures 4, 6:
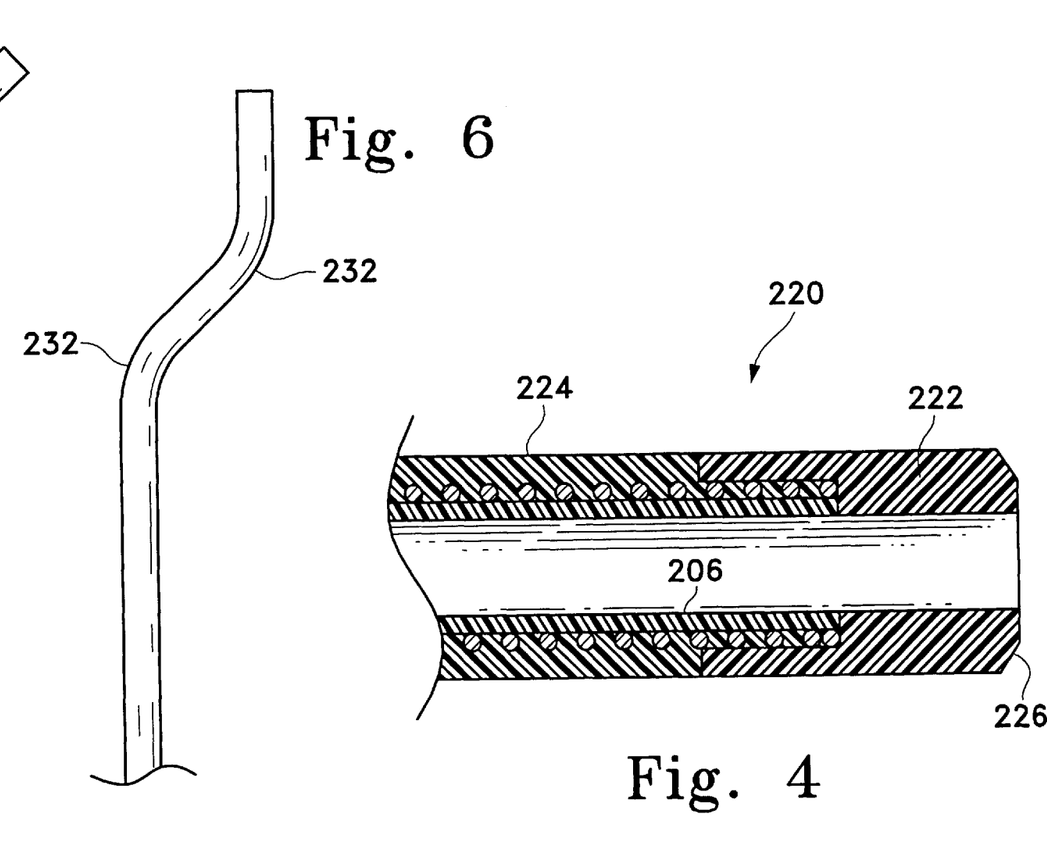
FIG. 4 shows, in magnification, a partial, side view, cross-section of a terminal section made using this invention.
FIGS. 5 and 6 show in magnified cross-section, various distal end sections of catheters.

FIG. 4 shows a highly desirable termination section (220). In this variation, the termination segment (222) overlaps the next more proximal portion (224) in a half-lap arrangement. The lubricious inner liner (206) terminates interior to the half-lap joint. A small chamfer (226) may be placed at the distal extremity so to allow a better passage of the device through blood vessels. Obviously chamfer (226) may be in other suitable shapes. The terminal portion (222) may be heat welded onto the remainder of the catheter assembly.

Figure 5:
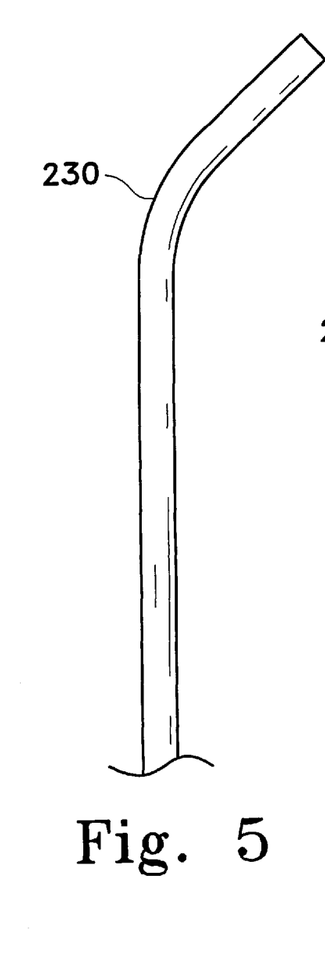

FIGS. 5 and 6 show desired shapes for the terminal regions of the inventive catheter. For instance, in FIG. 5 is shown a catheter which has been molded so that it has a radiused 45° turn near to its distal end. Similarly, FIG. 6 shows a pair of radiused turns to produce a catheter having a specific end configuration. It is within the scope of this invention that any variation of distal tip be accommodated to this structure. Because of the slightly harder terminal tip, the more proximal portions are used to progress the catheter further into the vasculature. Consequently, these tips are of more use in this inventive catheter than are others known in the art.

Figure 7:
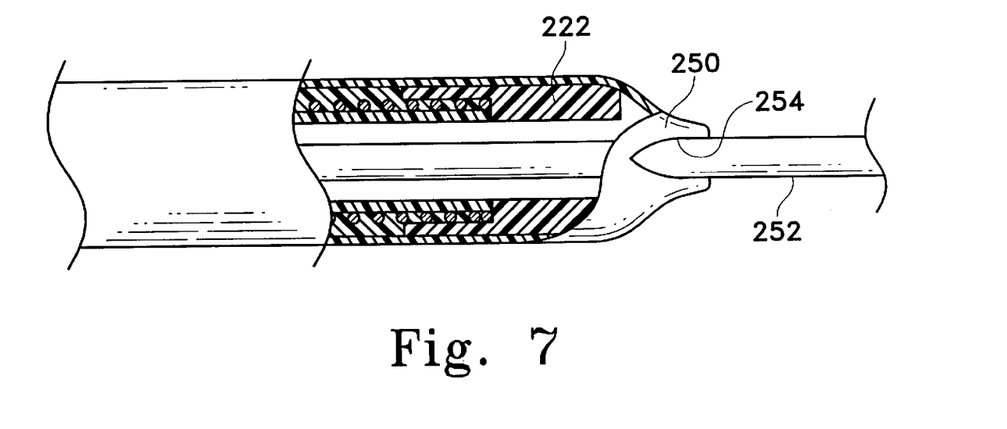
FIG. 7 shows, in magnification, a partial, side view, cross-section of a terminal section having a blood-control tip.

FIG. 7 shows a further variation of the invention in which the catheter device shown in any of the preceding Figures is covered with an outer tubing (250) which "necks down" distally of the terminal section (222) and fits tightly about micro-catheter (252). The outer covering (250) may be made of, e.g., a shrink-wrap material such as irradiated and oriented polyethylene, which has been shrunk onto the shaft of the catheter assembly. The variation shown in FIG. 7 has one or more slits (254) which operate as "one-way" valves against the micro-catheter (252) outer surface. This valving region prevents the body fluids from flowing into the catheter yet allows fluids such as radio-opaque materials to flow outwardly. The outer covering (250) may extend proximally up the catheter as long as is convenient.

Figure 8:
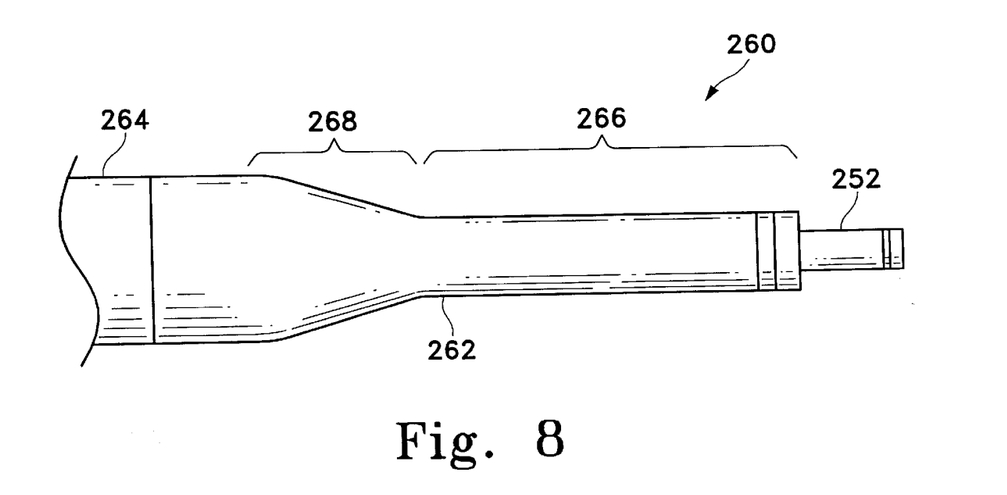
FIG. 8 shows in magnified cross-section, a tapered distal end section of a catheter made according to this invention.

FIG. 8 shows still another variation (260) of the inventive guide catheter assembly. In this variation (260), the micro-catheter (252) is shown extending from the distal end of the guide catheter (260). The terminal section (262) in this variation is quite extensive. The polymer making up the terminal section (262) is preferably the same hardness as is the next more proximal section (264). As may be seen in the drawing, the terminal section (262) has a narrow diameter section (264) and a tapered section (268). The inner lumen of narrow diameter section (266) fits closely about the outer diameter of microcatheter (252), e.g., with a clearance of 0.002" or so. Radio-opaque materials may be ejected through the end of the catheter assembly in the annular space outside the micro-catheter (252). In this way, radio-opaque fluids may also be ejected through the hole to improve visibility of the vessel. As was the case with the variations above, the braid reinforced sections are only to be found proximal of the terminal section, e.g., beginning in the section (264).

Although this invention has been described with reference to preferred embodiments and examples, those having ordinary skill in this art will recognize that changes may be made in form and detail without departing from the spirit and scope of the invention as found in the claims which follow.

We claim as our invention:

1. An intravascular guiding catheter comprising:

an elongate, tubular shaft formed from at least two tubular shaft members, said elongate, tubular shaft including:
   a.) a distal shaft member formed of an outer polymeric material having a braided reinforcing layer embedded therein and lined with an inner lubricious polymeric material and having a distal end,
   b.) a terminal shaft member formed of a polymeric material, free of braided reinforcing, having a wall and a lumen therethrough, and secured to said distal shaft member and located distally of said distal shaft member,
wherein the hardness of the polymeric material of said terminal shaft member is equal to or harder than the outer polymeric material of said distal shaft member, and
   c.) a proximal section, proximally adjacent said distal shaft member said proximal section being stiffer than said distal shaft member.

2. The catheter of claim 1 wherein the braided reinforcing layer comprises a stainless steel.

3. The catheter of claim 1 wherein the braided reinforcing layer comprises a superelastic alloy.

4. The catheter of claim 1 wherein the hardness of the polymeric material of said terminal shaft member is equal to the outer polymeric material of said distal shaft member.

5. The catheter of claim 1 wherein the hardness of the polymeric material of said terminal shaft member is harder than the outer polymeric material of said distal shaft member.

6. The catheter of claim 1 wherein the terminal shaft member and the distal shaft member each have diameters and the diameter of the terminal shaft member is smaller than the diameter of the distal shaft member.

7. An intravascular guiding catheter comprising:

an elongate, tubular shaft formed from at least two tubular shaft members, said elongate, tubular shaft including:
   a.) a primary midshaft member proximally adjacent a distal shaft member having an outer polymeric covering, and said primary midshaft member having an outer covering comprising a material harder than a material forming the outer polymeric covering of said distal shaft member,
   b.) said distal shaft member having a distal end and formed of the outer polymeric covering having a braided reinforcing member embedded therein and lined with an inner lubricious polymeric material, and
   c.) a terminal shaft member formed of a polymeric material, free of braided reinforcing, having a wall and a lumen therethrough, and secured to said distal shaft member and located distally of said distal shaft member,
wherein the hardness of the polymeric material of said terminal shaft member is equal to or harder than the outer polymeric covering of said distal shaft member.

8. The catheter of claim 7 wherein the elongate shaft further comprises a secondary midshaft member proximally adjacent said primary midshaft member and having an outer covering layer with a hardness greater than the outer covering of said primary midshaft member.

9. The catheter of claim 8 wherein the elongate shaft further comprises a proximal shaft member proximally adjacent said secondary midshaft member and having an outer covering harder than the outer covering layer of the secondary midshaft member.

10. The catheter of claim 9 wherein the braided reinforcing member extends continuously from the proximal shaft member to the distal end of the distal shaft member.

11. The catheter of claim 9 wherein each of the distal shaft member, primary midshaft member, secondary midshaft member, and the proximal shaft member contains the braided reinforcing member which is not continuous between such members.

12. The catheter of claim 7 wherein the braided reinforcing member comprises a stainless steel.

13. The catheter of claim 7 wherein the braided reinforcing member comprises a superelastic alloy.

14. The catheter of claim 7 wherein the hardness of the polymeric material of said terminal shaft member is equal to the outer polymeric covering of said distal shaft member.

15. The catheter of claim 7 wherein the hardness of the polymeric material of said terminal shaft member is harder than the outer polymeric covering of said distal shaft member.

16. The catheter of claim 7 wherein the terminal shaft member and the distal shaft member each have diameters and the diameter of the terminal shaft member is smaller than the diameter of the distal shaft member.

* * * * *